US011052205B2

(12) United States Patent
Mazhar et al.

(10) Patent No.: US 11,052,205 B2
(45) Date of Patent: Jul. 6, 2021

(54) DEVICES AND METHODS FOR DELIVERING FLUID TO A NASAL CAVITY

(71) Applicant: Neosinus Health Inc, Raleigh, NC (US)

(72) Inventors: Kashif Mazhar, Raleigh, NC (US); Magda R. Pugh, Raleigh, NC (US); Michael John Clare, Sylva, NC (US)

(73) Assignee: Neosinus Health Inc, Raleigh, NC (US)

( * ) Notice: Subject to any disclaimer, the term of this patent is extended or adjusted under 35 U.S.C. 154(b) by 108 days.

(21) Appl. No.: 16/437,551

(22) Filed: Jun. 11, 2019

(65) Prior Publication Data

US 2020/0390989 A1 Dec. 17, 2020

(51) Int. Cl.
*A61M 15/08* (2006.01)
*A61M 15/00* (2006.01)
*A61M 11/02* (2006.01)

(52) U.S. Cl.
CPC .......... *A61M 15/08* (2013.01); *A61M 15/009* (2013.01); *A61M 11/02* (2013.01); *A61M 2210/0618* (2013.01); *A61M 2210/0681* (2013.01)

(58) Field of Classification Search
CPC .............. A61M 15/08; B05B 11/0091; B05B 11/0094; B05B 1/14; B05B 1/1636; B05B 1/1672
See application file for complete search history.

(56) References Cited

U.S. PATENT DOCUMENTS

| | | | |
|---|---|---|---|
| 4,444,560 A | 4/1984 | Jacklich | |
| 4,940,061 A | 7/1990 | Terwilliger et al. | |
| 5,244,458 A | 9/1993 | Takasu | |
| 5,249,583 A | 10/1993 | Mallaby | |
| 5,601,572 A | 2/1997 | Middleman et al. | |
| 5,935,098 A | 8/1999 | Blaisdell et al. | |
| 7,824,436 B2 | 11/2010 | Barbut et al. | |
| 8,721,699 B2 | 5/2014 | Barbut et al. | |
| 8,932,339 B2 | 1/2015 | Harikrishna et al. | |
| 9,358,150 B2 | 6/2016 | Rozenberg et al. | |
| 10,252,038 B2 | 4/2019 | Pugh et al. | |
| 2002/0062119 A1 | 5/2002 | Zadno-Azizi | |
| 2004/0167473 A1 | 8/2004 | Moenning | |
| 2004/0267154 A1 | 12/2004 | Sutton et al. | |

(Continued)

FOREIGN PATENT DOCUMENTS

WO 2009049823 A1 4/2009

*Primary Examiner* — Deanna K Hall
(74) *Attorney, Agent, or Firm* — Coats & Bennett, PLLC

(57) ABSTRACT

Devices and methods for delivering fluid from a container to the nasal cavity. The device includes a selector and a nozzle that are connected together and rotatable relative to each other. The device includes a curve to overcome anatomical barriers and one or more openings to provide for effective distribution when delivering the fluid to the nasal cavity. The selector includes an opening that aligns with a corresponding opening in a container that holds the fluid. The nozzle includes a first passage with one or more openings on a first lateral side, and a second passage with one or more openings on an opposing second lateral side. The selector and nozzle can be positioned at a first and second rotational positions to selectively deliver the fluid through the first and second passages to the nasal cavity.

19 Claims, 12 Drawing Sheets

(56) References Cited

U.S. PATENT DOCUMENTS

| | | |
|---|---|---|
| 2006/0207596 A1 | 9/2006 | Lane |
| 2006/0210605 A1 | 9/2006 | Chang et al. |
| 2007/0213671 A1 | 9/2007 | Hiatt |
| 2008/0086165 A1 | 4/2008 | Lyon et al. |
| 2008/0125746 A1 | 5/2008 | Shapland et al. |
| 2009/0198216 A1 | 8/2009 | Muni et al. |
| 2010/0286616 A1 | 11/2010 | Baroud |
| 2012/0035501 A1 | 2/2012 | Landrigan et al. |
| 2013/0274711 A1 | 10/2013 | O'Day |
| 2014/0058353 A1 | 2/2014 | Politis et al. |
| 2014/0083424 A1 | 3/2014 | Hoekman et al. |
| 2014/0163530 A1 | 6/2014 | Frenkel |
| 2014/0276656 A1 | 9/2014 | Bian et al. |
| 2015/0038817 A1 | 2/2015 | Richter et al. |
| 2015/0104331 A1 | 4/2015 | Dye |
| 2015/0290421 A1 | 10/2015 | Glickman et al. |
| 2015/0297845 A1 | 10/2015 | Shahaf et al. |
| 2016/0228685 A1 | 8/2016 | Pugh et al. |
| 2019/0083741 A1 | 3/2019 | Pugh et al. |
| 2019/0160238 A1 * | 5/2019 | Al-Jarba ............... B05B 1/1636 |

* cited by examiner

DEVICES AND METHODS FOR DELIVERING FLUID TO A NASAL CAVITY

BACKGROUND

The nasal cavity comprises a variety of surfaces that correspond to anatomic structures directly and indirectly serving various respective biological functions. Generally, the nasal cavity is divided vertically by a wall of cartilage called the septum. On each side of the septum is a nostril through which the nasal cavity can be accessed. Opposite the septum, on each lateral side of the nasal cavity, are a series of turbinates (also known as concha). Each series comprises an inferior, middle, and superior turbinate, as one goes in a posterior direction from the nostrils, through the nasal cavity, towards the throat. These turbinates are a series of bony ridges that protrude into the nasal cavity. The maxillary, anterior ethmoid, and frontal sinuses drain into the nasal cavity from under the middle turbinate, which is above the inferior turbinate.

In order to treat these anatomic structures within the nose, therapeutic fluids can be topically applied to their corresponding surfaces via a process called local intranasal drug delivery. Such fluids for example, include saline, antihistamines, decongestants, and corticosteroids, which may be helpful in irrigating nasal passages, treating allergies, relieving nasal congestion, and treating inflammation, respectively. The fluids can also include one or more drugs. Additionally, the nasal mucosa can serve as a non-invasive drug delivery pathway to the brain via nose-to-brain intranasal drug delivery and to the systemic circulation via systemic intranasal drug delivery, which overcomes anatomical and physiological barriers such as the blood-brain barrier and first-pass metabolism, respectively. Collectively, the intranasal drug delivery provides an optimized and targeted method for delivering therapies, including monoclonal antibody therapies, that are represented by therapeutic classes such as respiratory, central nervous system, gastrointestinal, dermatological, and others.

To deliver these fluids to various surfaces in the nasal cavity, a spray bottle is often used. To use the spray bottle, a patient typically inserts a nozzle through their nostril and ejects fluid from the nozzle in a haphazard and indiscriminate fashion. While haphazardly and indiscriminately dispensing fluid in this fashion tends to result in at least some fluid being applied to an appropriate surface within the nasal cavity, such an approach is inefficient at best. Indeed, a large percentage of the fluid delivered by this method is often wasted by being applied to surfaces for which the fluid can deliver little to no therapeutic value.

SUMMARY

One aspect is directed to a device to deliver fluid from a container to a nasal cavity. The device includes a selector with a receptacle sized to extend over a top of the container and having an opening sized to align with an outlet in the container. A nozzle is connected to the selector. The nozzle includes: first and second passages that are spaced apart and that each include a proximal end towards the selector and an opposing distal end; one or more first openings in communication with the first passage and positioned at a first lateral side of the nozzle; and one or more second openings in communication with the second passage and positioned at an opposing second lateral side of the nozzle. The nozzle is rotatable relative to the selector between first and second positions. The first position includes the first passage aligned with the outlet in the container to receive the fluid from the container and deliver the fluid through the first passage and out through the one or more first openings and with the second passage positioned away from the outlet. The second position includes the second passage aligned with the outlet in the container to receive the fluid from the container and to deliver the fluid through the second passage and out through the second openings and with the first passage positioned away from the outlet.

In another aspect, the first and second passages are fixedly positioned relative to each other within the nozzle.

In another aspect, the nozzle includes a base that connects to the selector and an extension that extends outward from the base in a direction away from the selector with the first and second passages extending through the extension.

In another aspect, the extension includes an elongated sectional shape with a major axis and a minor axis with the first and second passages being positioned along the major axis.

In another aspect, the selector includes a top face and a side wall that form the receptacle with the opening extending through the side wall and the top face.

In another aspect, the opening extends along the top face inward from the side wall and terminates at a back edge with the back edge being positioned away from a center point of the top face.

In another aspect, flanges extend from each of the selector and the nozzle and engage together to rotatably connect the selector to the nozzle.

In another aspect, filler rods are positioned within each of the first passage and the second passage with the filler rods including smaller sectional sizes than the first passage and the second passage to limit an open area of the first passage and the second passage.

In another aspect, the nozzle has a curved section with a length of 2-10 centimeters and has 30°-90° of curvature.

In another aspect, the length of the curved section is between 3.75-4.25 centimeters and the curvature is 60°-80°.

In another aspect, a recess extends into a distal end of the nozzle and the distal ends of the first and second passages terminate in the recess and are spaced inward from the distal end of the nozzle.

One aspect is directed to a device to deliver fluid from a container to a nasal cavity. The device includes a selector and a nozzle that are connected together and configured to connect to the container. The selector includes an opening configured to align with an outlet in the container. The nozzle includes: a base and an outwardly-extending extension with the extension including a length measured between a proximal end at the base and an opposing distal end; a first passage that extends along the extension and includes a first inlet at the base and first openings that face just towards the distal end and a first lateral side of the extension to expel the fluid from the first openings and to prevent the fluid from being expelled from a second lateral side of the extension; a second passage spaced away from the first passage and that extends along the extension and includes a second inlet at the base and second openings that face just towards the distal end and the second lateral side of the extension to expel the fluid from the second openings and to prevent the fluid from being expelled from the first lateral side of the extension. The nozzle is rotatable relative to the selector between a first position to align the first passage with the outlet in the container and the second being misaligned with the outlet, and a second position to align the second passage with the outlet in the container and the first passage being misaligned with the outlet.

In another aspect, one of the first openings extends through the distal end of the extension and one of the second openings extends through the distal end of the extension.

In another aspect, a recess extends into a distal end of the nozzle and the first and second passages terminate in the recess and are spaced inward from the distal end of the nozzle.

In another aspect, the first position includes the first inlet aligned with the outlet in the container to receive the fluid from the container and deliver the fluid through the first passage and out through the first openings, and the second position includes the second inlet aligned with the outlet in the container to receive the fluid from the container and to deliver the fluid through the second passage and out through the second openings.

In another aspect, the selector includes a top face and a side wall that extends outward from the top face with the opening including a slot that extends through the side wall and a portion of the top face.

In another aspect, the first passage and the second passage extend along the length of the extension in a side-by-side arrangement.

In another aspect, the first passage and the second passage are fixedly positioned within the extension and remain stationary relative to each other in each of the first position and the second position.

In another aspect, the extension includes an elongated sectional shape with a major axis and a minor axis with the first and second passages being positioned along the major axis.

In another aspect, filler rods are positioned in the first and second passages to reduce an open interior space within the first and second passages.

One aspect is directed to a method of delivering fluid from a container to a nasal cavity. The method includes rotating a nozzle relative to a selector to a first position and aligning a first passage of the nozzle with an outlet of the container while the nozzle is connected to the selector and both the nozzle and the selector are connected to the container. The method includes directing the fluid that is expelled from the container through the first passage that extends along the length of the nozzle and out through first openings that face outward towards a distal end and a first lateral side of the nozzle. The method includes while in the first position positioning a second passage of the nozzle away from the outlet and preventing the fluid from being moved into the second passage and preventing the fluid from being expelled outward from a second lateral side of the nozzle. The method includes rotating the nozzle relative to the selector to a second position and aligning a second passage of the nozzle with the outlet of the container while the nozzle is connected to the selector and both the nozzle and the selector are connected to the container. The method includes directing the fluid that is expelled from the container through the second passage that extends along the length of the nozzle and out through second openings that face outward towards the distal end and a second lateral side of the nozzle. The method includes while in the second position positioning a first passage of the nozzle away from the outlet and preventing the fluid from being moved into the first passage and preventing the fluid from being expelled outward from the first lateral side of the nozzle.

In another aspect, the method includes aligning a spout at the outlet of the container within a slot in the selector and connecting the selector and the nozzle to the container with the spout extending beyond the selector and being contained within the nozzle.

In another aspect, the method includes positioning a first filler rod within the first passage and reducing a size of the first passage prior to connecting the selector and the nozzle to the container and positioning a second filler rod within the second passage and reducing a size of the second passage prior to connecting the selector and the nozzle to the container.

In another aspect, the method includes aligning the selector relative to the container with the outlet being positioned laterally away from a centerline of the selector.

In another aspect, the method includes laterally connecting the selector to the container and inserting a spout of the container through a slot in the selector.

In another aspect, the method includes expelling the fluid from each of the first and second passages into a recess that extends into the distal end of the nozzle.

The various aspects of the various embodiments may be used alone or in any combination, as is desired.

DETAILED DESCRIPTION

Figure 1:
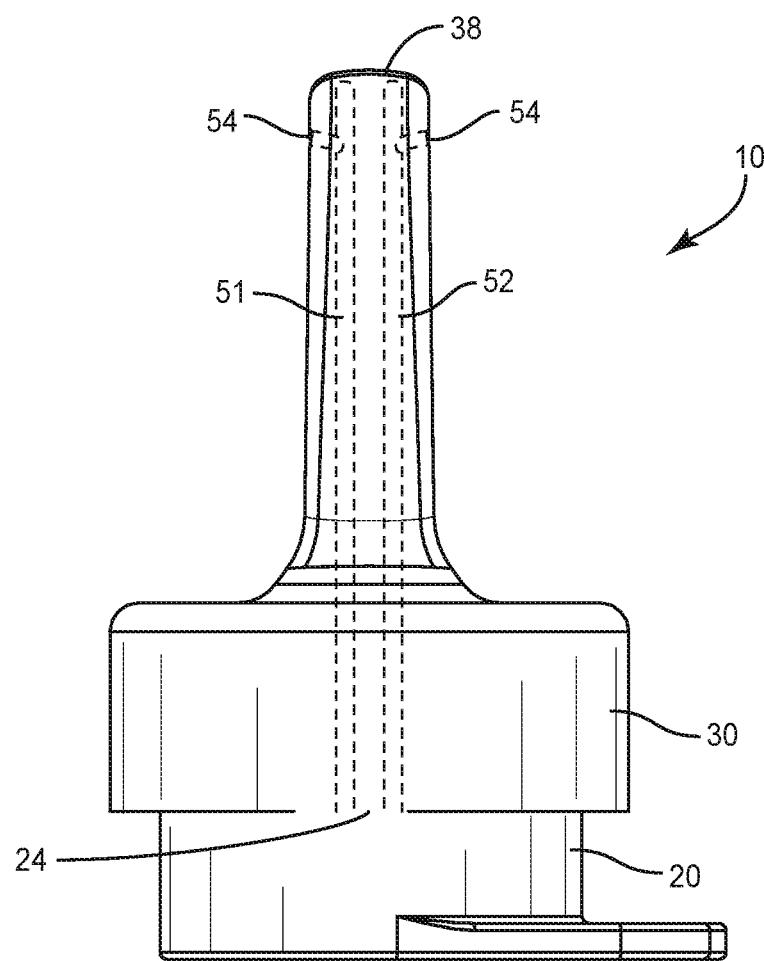
FIG. 1 is a schematic view of a device to deliver fluid to a nasal cavity.

The present application is directed to devices and methods for delivering fluid from a container to the nasal cavity. FIG. 1 schematic illustrates a device 10 for delivering fluid. The device 10 includes a selector 20 and a nozzle 30 that are connected together and rotatable relative to each other. The selector 20 and nozzle 30 are further configured to be connected to a container that holds the fluid (not illustrated in FIG. 1). The selector 20 includes an opening 24 that aligns with a corresponding opening in the container. The nozzle 30 includes a first passage 51 with one or more openings 54 on a lateral side, and a second passage 52 with one or more openings 54 on an opposing lateral side. The selector 20 and nozzle 30 can be positioned at a first rotational position with the first passage 51 aligned with the opening 24 to receive the fluid and direct it through the one or more openings 54 on the first lateral side. The selector 20 and nozzle 30 can be positioned at a second rotational position with the second passage 52 aligned with the opening 24 to receive and direct the fluid through the one or more openings 54 on the second lateral side. One or more openings can also be positioned at a distal end 38 to direct fluid distally outward in one or both of the first and second positions.

Figure 2:
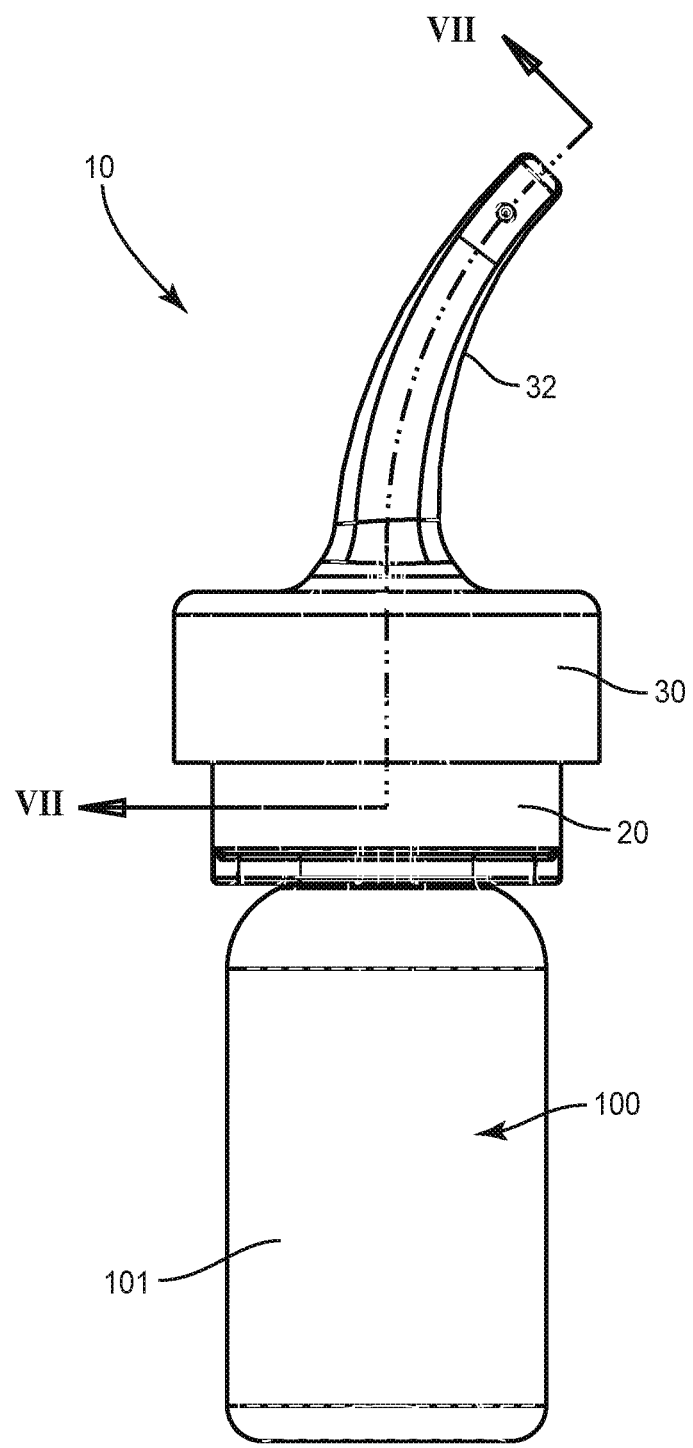
FIG. 2 is a side view of a device connected to a container that holds a fluid.
Figure 3:
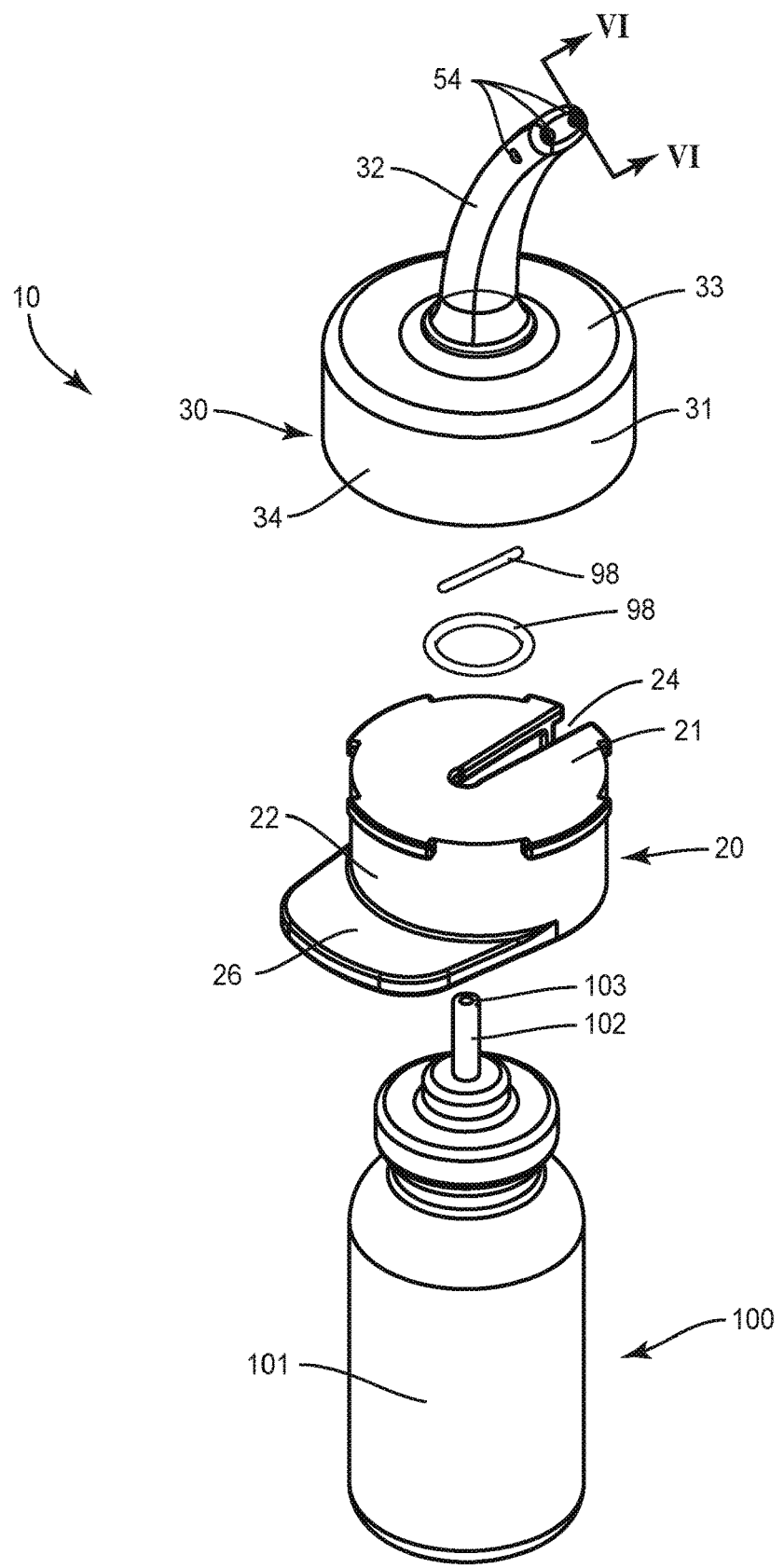
FIG. 3 is an exploded view of the device of FIG. 2.

FIG. 2 illustrates a side view of a device 10 connected to a container 100. FIG. 3 illustrates an exploded view of the device 10 and container 100. The device 10 includes a selector 20 that connects to the container 100. A nozzle 30 is connected to the selector 20 and extends outward from an opposing side away from the container 100. The nozzle 30 is sized to be inserted into the nasal cavity and direct the fluid.

The device 10 provides for dispensing and directing the fluid from the container 100 to selective positions within the nasal cavity. The fluid can be dispensed as a rinse or as a spray. The container 100 includes a body 101 with an enclosed interior that contains the fluid and an open end. An outlet 103 provides for outputting the fluid from the container 100. The outlet 103 can be positioned within a spout 102 that is connected to one end of the body 101. A tube (not illustrated) can be positioned within the interior of the body 101. A first end of the tube is attached at the outlet 103 and a second end is positioned in a lower section and/or bottom of the interior. The tube provides for collecting the fluid from the interior and moving it to the outlet 103.

The device 10 can contain a variety of different fluids and can include drugs to support local intranasal drug delivery, systemic intranasal drug delivery, and nose-to-brain intranasal drug delivery. Fluids include but are not limited to saline, antihistamines, decongestants, and corticosteroids. Drugs include but are not limited to therapies, including monoclonal antibody therapies, that are represented by therapeutic classes such as respiratory, central nervous system, gastrointestinal, dermatological, and others.

One or more gaskets 98 can be positioned to prevent the fluid from leaking. The gaskets 98 can include various shapes and sizes to accommodate the shape and dimensions of the device 10. FIG. 3 includes a first gasket 98 having an annular shape and a second gasket 98 have a straight rod-like shape. In one example, the gaskets 98 are positioned between the selector and the nozzle 30 to prevent fluid from leaking. The annular gasket 98 is positioned in the receptacle 36 in proximity to the proximal end 37 and the first and second passages 51, 52. The straight gasket 98 is positioned at the proximal end 37 between the first and second passages 51, 52 to prevent the fluid from inadvertently entering one of the passages 51, 52.

Figure 4:
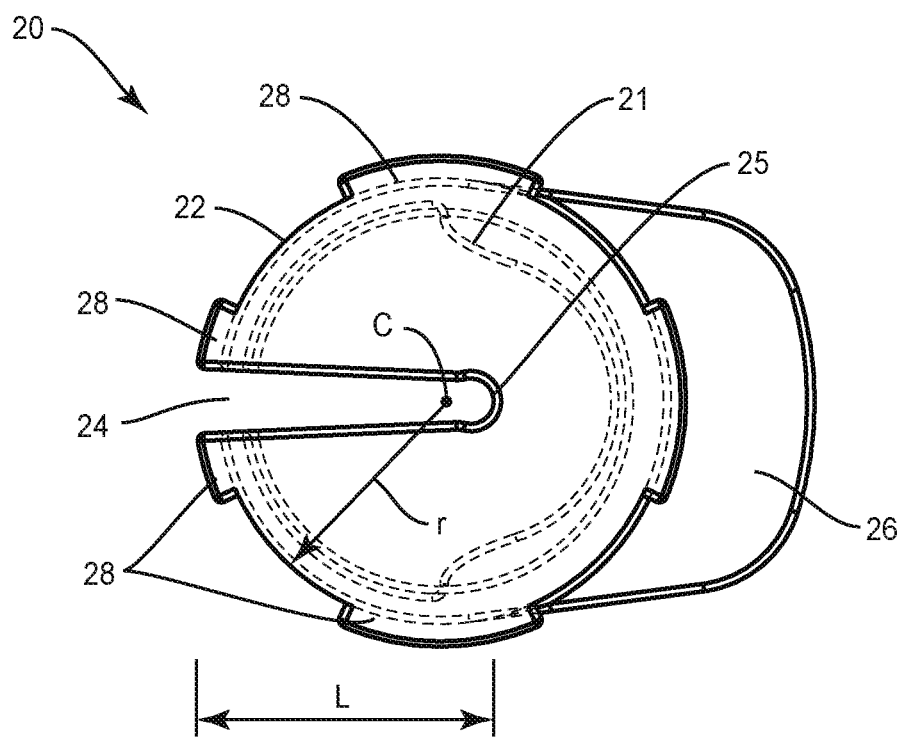
FIG. 4 is a top view of a selector.
Figure 5:
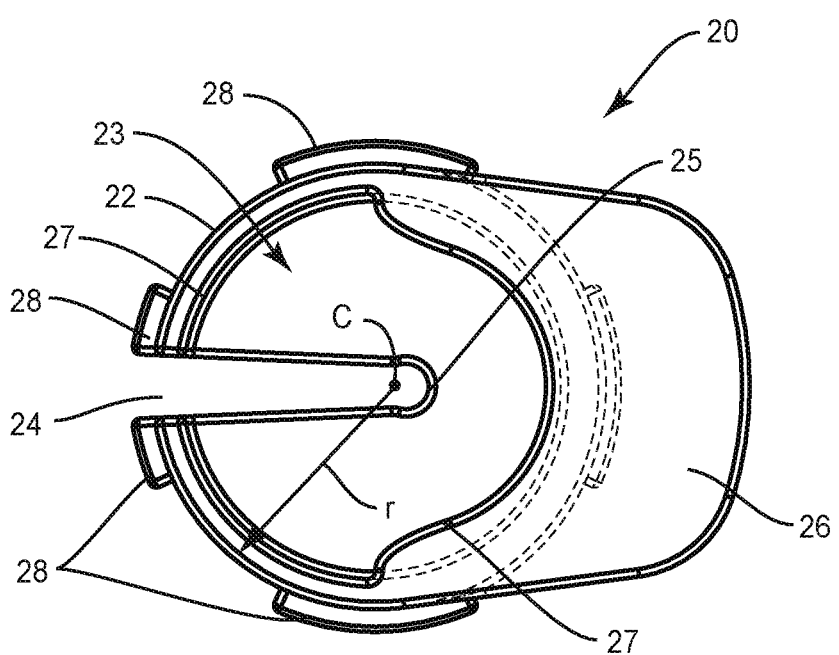
FIG. 5 is a bottom view of the selector of FIG. 4.

The selector 20 is configured to connect to the container 100. FIG. 4 illustrates a top view of the selector 20, and FIG. 5 illustrates a bottom view. The selector 20 includes a top face 21 and side wall 22 that form a receptacle 23. An opening 24 extends through a section of the top face 21 and is sized to receive the spout 102. The opening 24 can be isolated to just the top face 21. Additionally or alternatively, the opening 24 can be a slot that extends through a section of the top face 21 and the side wall 22. The slot can facilitate attaching the selector 20 to the container 100 as the selector 20 can be moved in a lateral direction and snap fit onto the container 100 with the spout 102 being received in the slot.

In a slot embodiment as illustrated in FIGS. 4 and 5, the slot opening 24 extends inward from the side wall 22. The opening 24 extends along the top face 21 and terminates at a back edge 25. The length L of the opening 24 measured between the side wall 22 and the back edge 25 can vary. The slot opening 24 is shaped and/or sized for the back edge 25 to be positioned away from a center line C that extends through the selector 20. In one design as illustrated in FIGS. 4 and 5, the top face 21 includes a substantially circular shape that has a radius r. The length L of the opening 24 is different than the radius r. In one design as illustrated in FIGS. 4 and 5, the length L of the opening 24 is greater than the radius r. Other designs can include the length L being less than the radius r. In another design, the slot opening 24 extends into the top face 21 at an angle away from the centerline line C and with the back edge 25 away from the centerline C.

A tab 26 extends outward from the side wall 22. In one design as illustrated in FIG. 3, the tab 26 is positioned at a bottom of the side wall 22 with the top face 21 positioned at a top of the side wall 22. The tab 26 can also be positioned at other locations along the height of the side wall 22. The tab 26 provides a surface for the user to apply a force to move the selector 20 towards the container 100, which is how the user directs the flow to the left or right, thus producing a unidirectional or multidirectional flow upwards through one or more openings 54 and in the direction selected. This force activates the container 100 and causes the fluid to be dispelled from the interior space of the body 101 and out through the outlet 103 and spout 102.

A shelf 27 extends radially inward from an inner side of the side wall 22. The shelf 27 provides for engaging with the spout 102 and/or body 101 of the container 100 to attach the selector 20. As illustrated in FIG. 5, the shelf 27 can be smaller at the opening 24, and can be larger away from the opening 24. As best illustrated in FIG. 5, the shelf 27 can be largest between the back edge 25 and side wall 22 away from the opening 24. This can coincide with the tab 26.

One of more flanges 28 can extend radially outward from an outer side of the side wall 22. The one or more flanges 28 provide for engaging with the nozzle 30. In one design, a series of flanges 28 are spaced apart by gaps and positioned at various spacings around the side wall 22. The flanges 28 can include the same or different shapes and/or sizes. In one design as illustrated in FIGS. 4 and 5, a pair of relatively small flanges 28 are positioned on opposing sides of the opening 24. Larger flanges 28 are spaced apart around a remainder of the side wall 22.

Figure 6:
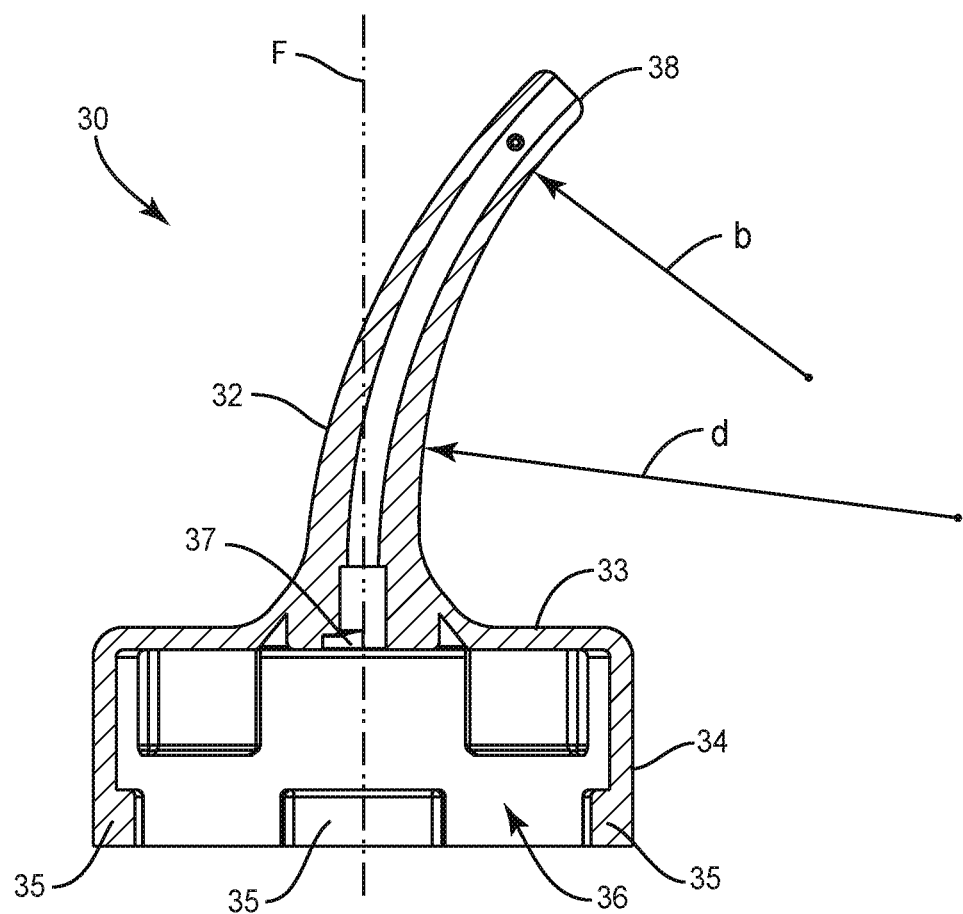
FIG. 6 is a section view of the nozzle of FIG. 3 cut along line VI-VI.

The nozzle 30 is attached to the selector 20. The nozzle 30 includes a base 31 that engages with the selector 20 and an elongated extension 32 for insertion into a nasal passage of the user. As illustrated in FIGS. 3 and 6, the base 31 includes a top wall 33 and a side wall 34 that extends outward in one direction around the periphery. The top wall 33 provides a surface for the user to apply a force to move the selector 20 and nozzle 30 toward the container 100, thus initiating the flow of fluid. The top wall 33 and side wall 34 form a receptacle 36 that receives the selector 20. One or more flanges 35 can extend radially inward from the side wall 34. The one or more flanges 35 engage with the selector 20 and/or the container 100 to attach the nozzle 30. In one design, the flanges 35 on the nozzle 30 engage with the flanges 28 on the selector 20 to connect the nozzle 30 to the selector 20. The circular sectional shape of the receptacle 36 provides for the nozzle 30 to be rotatable relative to the selector 20 to selectively position the nozzle 30 as various rotational positions.

The extension 32 extends outward from the base 31 away from the receptacle 36. The extension 32 includes a proximal end 37 at the top wall 33 and an opposing distal end 38. The extension 32 includes a curved shape that curves away from a centerline F of the base 31. As illustrated in FIG. 6, the curved shape results in the proximal end 37 being at or in closer proximity to the centerline F than the distal end 38. The curved shape can extend along the entire length of the extension 32 between the proximal and distal ends 37, 38. The curved shape can be lesser at the proximal end 37 with a smaller radius b and greater at the distal end 38 with a greater radius d. The extension 32 can also include other shapes as necessary to deliver the fluid to the nasal cavity. One design includes a straight shape. In one design, the extension 32 has a curved section with a length between 1-20 centimeters. In one specific design, the curved section has a length between 3-8 centimeters. In one design, the curved section has a shape with a curvature of between 30°-90°. In another design, the curvature is between 50°-80°. In one specific design, the curvature is between 60°-80°. In one specific design, the extension 32 has curved section with a length of between 3.75-4.25 centimeters and a curvature of between 67°-73°.

Figure 7:
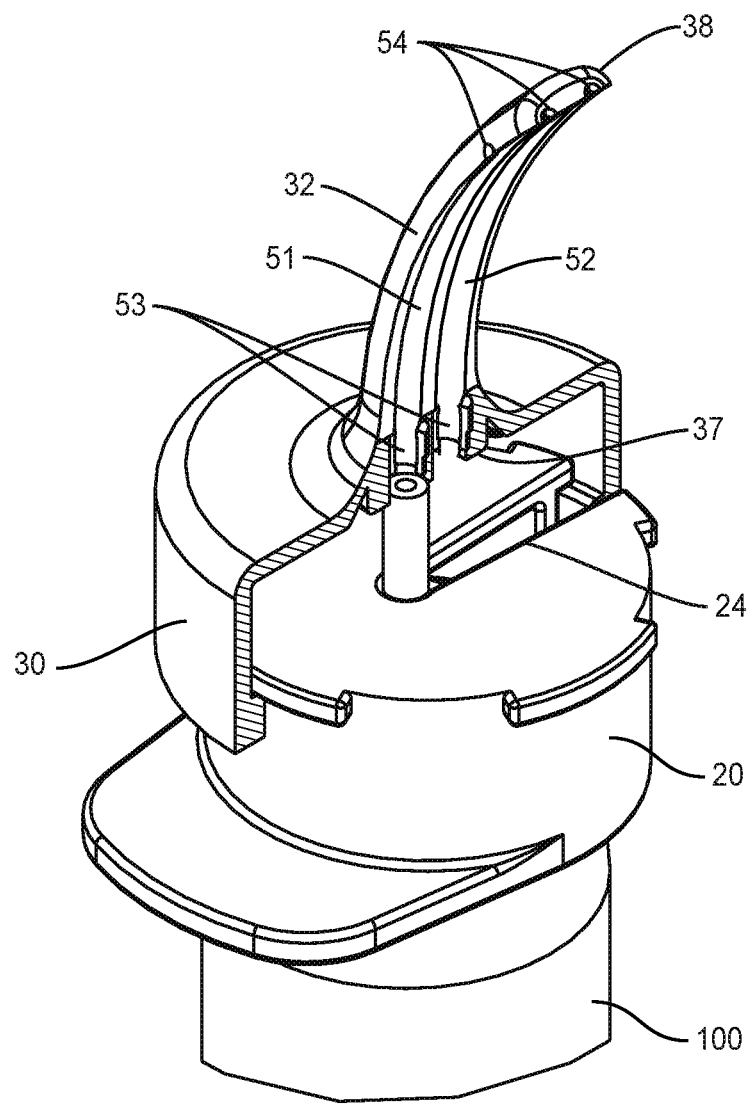
FIG. 7 is a section view of the nozzle of FIG. 2 cut along line VII-VII with a remainder of the device and a portion of the container in perspective.

As illustrated in FIG. 7, first and second passages 51, 52 extend through the extension 32. The passages 51, 52 are independent and separated along the extension 32. Further, the passages 51, 52 are fixed within the nozzle 30 and do not move relative to one another. Each passage 51, 52 includes an inlet 53 at the proximal end 37, and one or more openings 54. The one or more openings 54 can be positioned along lateral sides of the extension 32 away from the distal end 38. One or more of the openings 54 can extend through the distal end 38. In one design, one or more openings 54 are positioned along each lateral side of the extension 32, and two or more openings 54 are positioned at the distal end 38. The multiple openings 54 along different sides of the extension 32 provides for dispersing the fluid in multiple directions from each of the passages 51, 52. In one design, fluid can be dispersed from the first passage 51 along the distal end 38 and one lateral side, and from the second passage 52 along the distal end 38 and an opposing lateral side.

Figure 8:
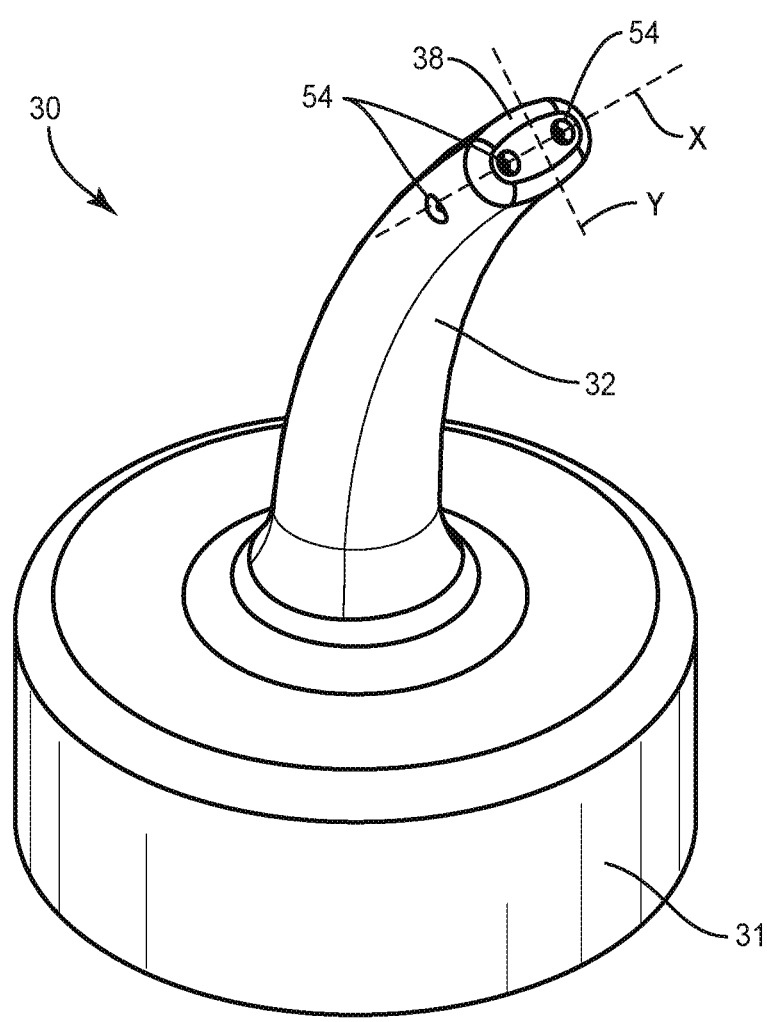
FIG. 8 is a perspective view of a nozzle.

As illustrated in FIG. 8, the extension 32 includes an elongated sectional shape that includes a major axis x and a minor axis y. This elongated shape accommodates the first and second passages 51, 52 that extend along the extension 32 in a side-by-side orientation. The elongated sectional shape further includes rounded corners to facilitate insertion into the nasal cavity.

Figure 8A:
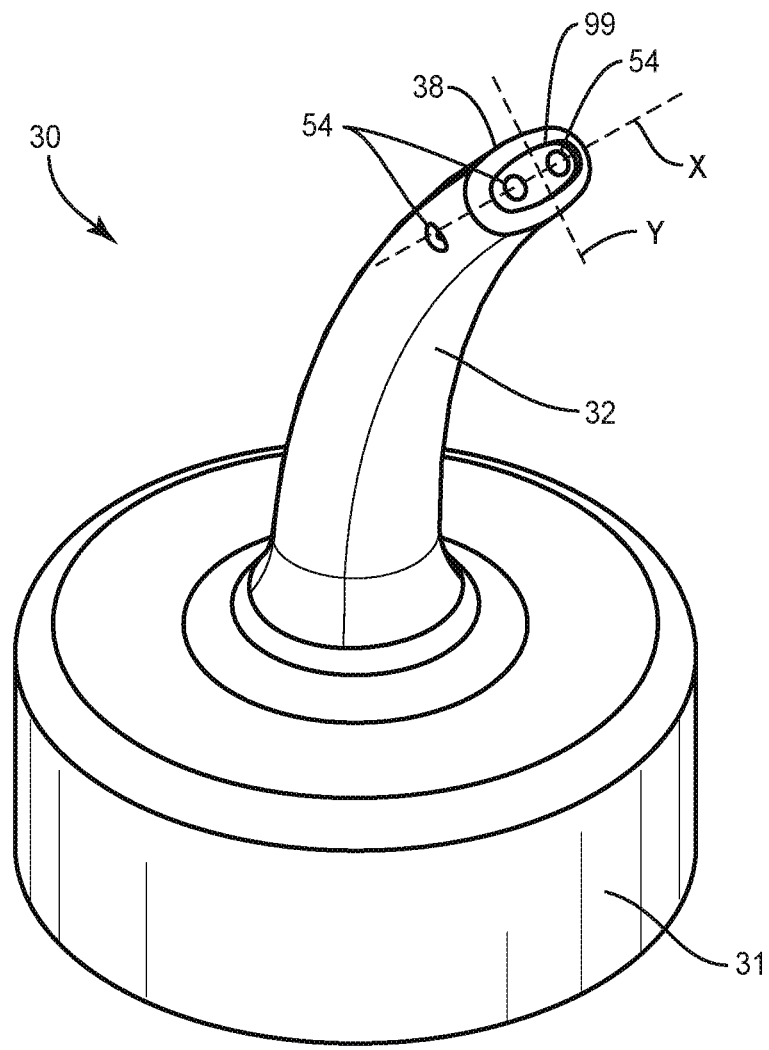
FIG. 8A is a perspective view of a nozzle.

In one example as illustrated in FIG. 8, the first and second passages 51, 52 extend the entire length of the extension 32 from the proximal end 37 to the distal end 38. As illustrated, each passage 51, 52 terminates at a separate opening 54 at the distal end 38. In another example as illustrated in FIG. 8A, a recess 99 extends into the distal end 38 of the extension 38. The recess can have a cupped shape with various depths. The distal end 38 at the recess 99 has rounded edges to facilitate insertion into the nasal cavity and to prevent damage to the nasal cavity that could be caused by sharper edges. Each passage 51, 52 terminates at a separate opening 54 that is positioned in the recess 99 and is spaced inward from the distal end 38.

The nozzle 30 is rotatably connected to the selector 20 and rotatable between a first position and a second position. FIG. 7 illustrates the nozzle 30 attached to the selector 20 and in the first position. This first position locates the inlet 53 of the first passage 51 with the outlet 103 in the spout 102 of the container 100. When the user applies a force to the container 100, the fluid is ejected from the outlet 103 of the spout 102 and enters into the first passage 51. The fluid moves along the length of the first passage 51 and is expelled through the first openings 54, either along just the first lateral side of the extension 32, or along just the lateral side and the distal end 38. Because the second passage 52 is not aligned with the outlet 103 of the spout 102 in the first position, the fluid is prevented from entering into the second passage 52. Thus, fluid is dispersed just to a limited section of the user's nasal cavity when in this first position.

The nozzle 30 can also be rotated relative to the selector 20 to a second position. The second position locates the inlet 53 of the second passage 52 with the outlet 103 in the spout 102 of the container 100. Fluid can be ejected from the outlet 103 of the spout 102 and into the second passage 52 and expelled through the openings 54 at either just the opposing lateral side, or just the opposing lateral side and the distal end 38. In the second position, the first passage 51 is positioned away from the outlet 103 of the spout 102 and the fluid is prevented from entering into the first passage 51.

The nozzle 30 can be positioned relative to the selector 20 in a third position. The third position can locate the inlets 53 of both the first passage 51 and the second passage 52 away from the spout 102. The third position can be an off or closed position when the user does not want fluid to be dispensed through the nozzle 30.

Figure 9:
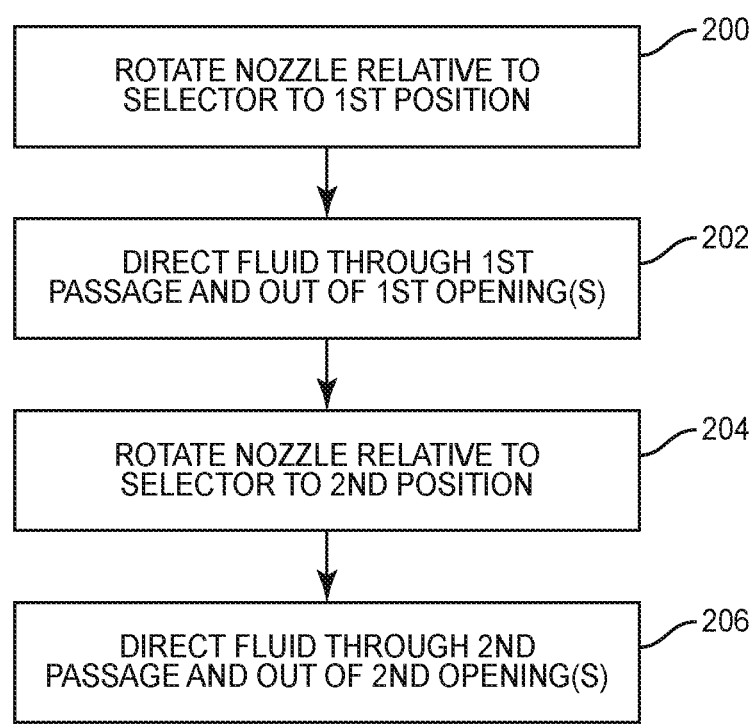
FIG. 9 is a flowchart diagram of a method of delivering fluid to a nasal cavity of a user.

FIG. 9 illustrates a method of using the device 10 to deliver fluid to the nasal passages. The method includes rotating the nozzle 30 relative to the selector 20 in a first direction to a first position (block 200). The first position aligns the first passage 51 of the nozzle 30 with the opening 24 of the selector 20. This also aligns the first passage 51 with the outlet 103 of the spout 102 that extends from the container 100. The movement of the nozzle 30 and selector 20 occurs while connected to the container 100.

The container 100 is activated and fluid from the container 100 is enters into the inlet 53 of the first passage 51 and through the first passage 51 and out through one or more first openings 54 (block 202). The one or more first openings 54 can be positioned just along a first lateral side of the extension 32, or along the first lateral side and the distal end 38. In this first position, the second passage 52 is positioned away from the outlet 103 of the spout 102. This prevents the fluid from entering into the second passage 51.

The nozzle 30 can be rotated relative to the selector 20 in a second direction to a second position (block 204). The second position aligns the second passage 52 of the nozzle 30 with the opening 24 of the container 20 while the nozzle 30 is connected to the selector 20 and both the nozzle 30 and the selector 20 are connected to the container 100. The second position also aligns the inlet 53 of the second passage 52 with the outlet 103 of the spout 102 of the container 100.

While in the second position, the container 100 can be activated and the fluid from the container 100 enters into the inlet 53 of the second passage 52 and moves through the second passage 52 and out through the one or more second openings 54 (block 206). The one or more second openings 54 can be positioned along just the opposing second lateral side of the extension 32, or along both the second lateral side and the distal end 38. In the second position, the first passage 51 is positioned away from the outlet 103 of the spout 102. This prevents the fluid from entering into the first passage 51.

Activation of the container 100 to dispel the fluid can occur in various manners. One design includes the user applying a downward force on the tab 26. The interior of the container 100 can be pressurized and this downward force causes the outlet 103 to open thus allow for the pressurized fluid to move out through the outlet 103. In another design, the downward force on the top wall 33 forces air into the interior of the container 100. This introduced air displaces the fluid which is driven out through the outlet 103. Another design provides for activation to be caused by the user squeezing the container 100. This delivery forces the fluid from the interior of the container through the outlet 103. Releasing the container 100 causes the container to move back to its original shape. Air is drawn into the interior of the container (such as through one or more openings in the selector 20).

In one design, the first passage 51 and second passage 52 are sized to deliver the fluid to the nasal passages. The sectional sizes of the passages 51, 52 can be the same or can be different. In one design, the passages 51, 52 include an inner diameter of 2.18 mm at the distal end 38. In another design, the inner diameter is within a range of 0.05 mm-5.0 mm. Filler rods 70 can be positioned in one or both of the passages 51, 52. When present, the filler rods 70 reduce the cross-sectional area of the passages 51, 52. In this regard, the filler rods 70 may be useful for accelerating the fluid through the passages 51, 52. Although a similar effect may be obtained by sizing the passages 51, 52 more narrowly and omitting the filler rods 70, small diameter passages 51, 52 may be difficult to manufacture, thereby making wider diameter passages in combination with the filler rods 70 advantageous in some circumstances.

Figure 10:
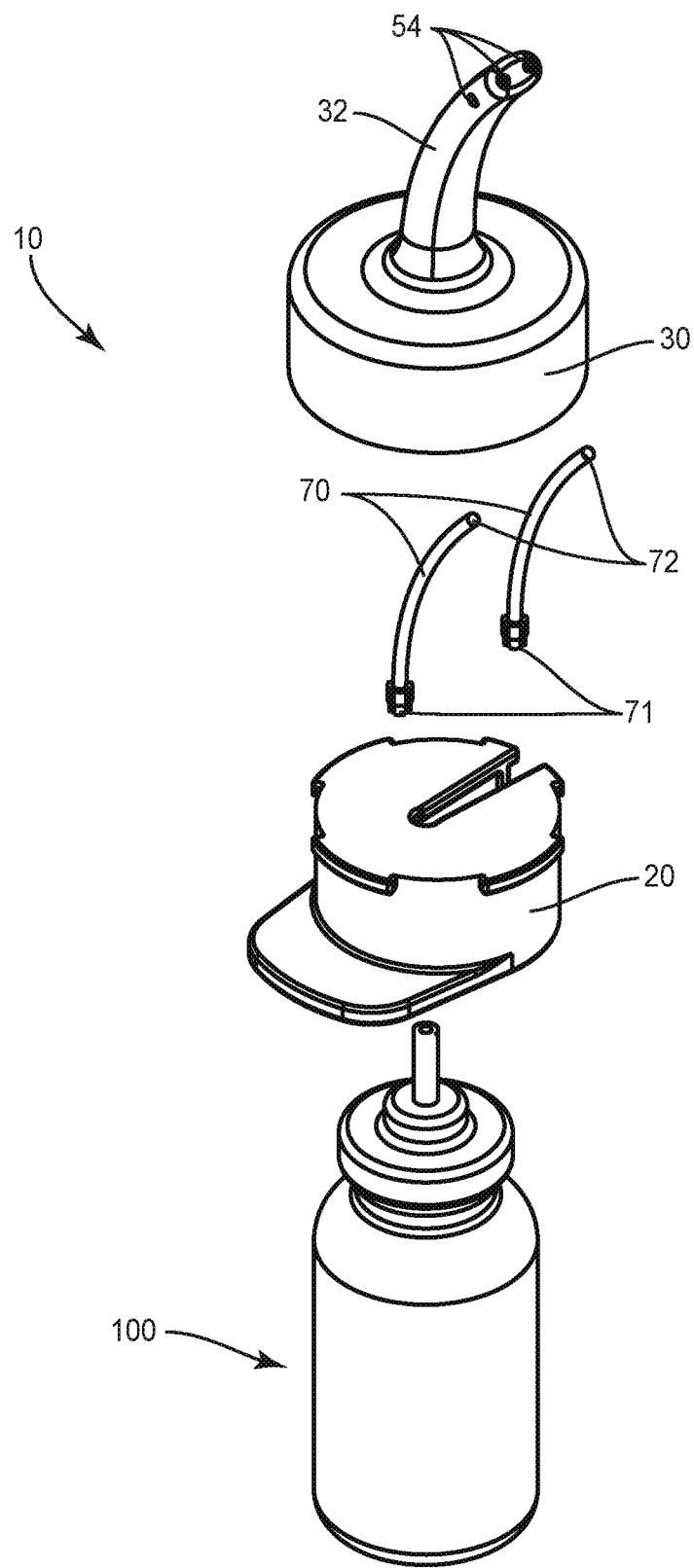
FIG. 10 is an exploded view of a device to deliver fluid to a nasal cavity.

As illustrated in FIG. 10, the filler rods 70 are sized to be positioned within one or both of the passages 51, 52. In these designs, the passages 51, 52 are manufactured with a larger sectional size than needed for delivering the fluid. To reduce the size, filler rods 70 are positioned in the passages 51, 52. The filler rods 70 include a smaller sectional size than the passages 51, 52 and thus reduce the effective size to deliver a smaller amount of the fluid.

The filler rods 70 include a first end 71 and opposing second end 72. The length of the filler rods 70 measured between the ends 71, 72 can be the same or smaller than the length of the passages 51, 52. In one design, the filler rods 70 extend along the passages 51, 52 with the ends 72 positioned proximally inward from the openings 54 on the lateral sides of the extension 32.

Figure 11:
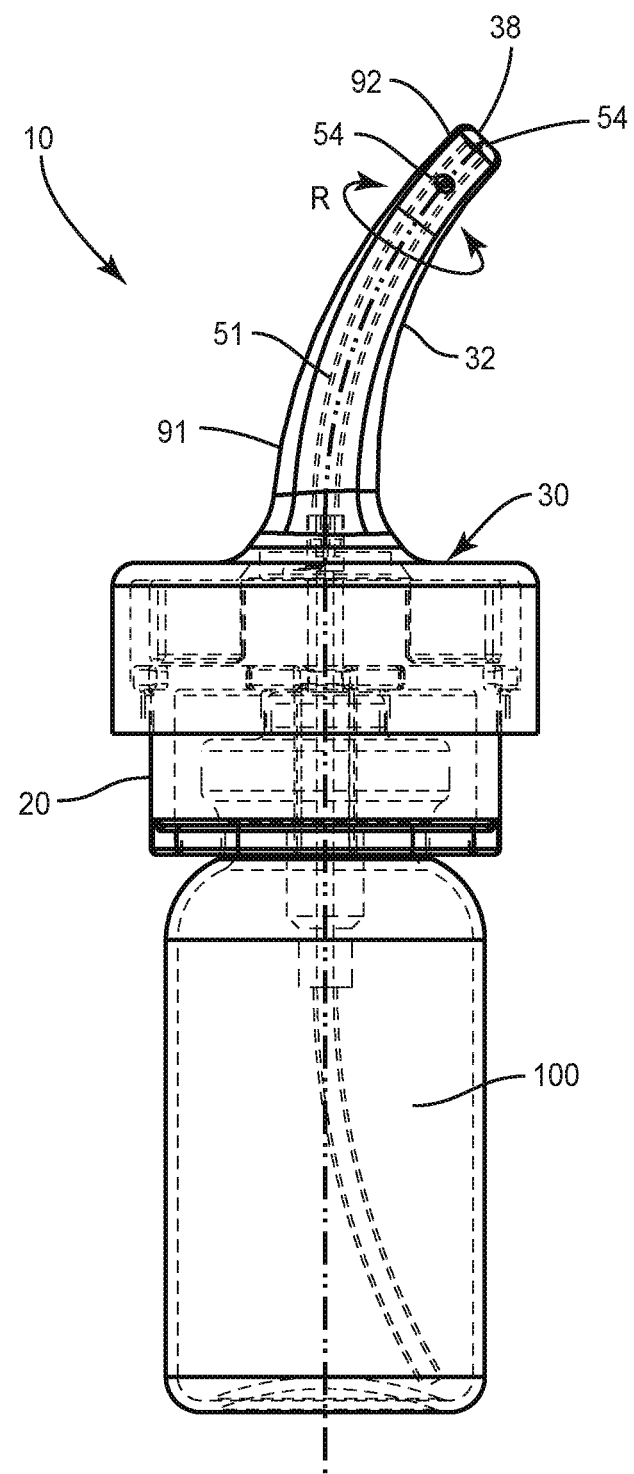
FIG. 11 is a perspective view of a device to deliver fluid to a nasal cavity.

FIG. 11 includes a device 10 with a selector 20 and a nozzle 30 that are connected together and also configured to be connected to the container 100. The selector 20 includes an opening 24 (not illustrated in FIG. 11) that receives the fluid from the container 100 as disclosed above. The nozzle 30 includes an extension 32 that includes a proximal section 91 and a distal section 92. The distal section 92 is rotatable relative to the proximal section 91 as illustrated by arrows R-R. A single passage 51 extends through the extension 32 including both the proximal section 91 and the distal section 92. One or more openings 54 are positioned on just one lateral side of the distal section 92. One or more openings 54 can also be positioned on the distal end 38.

In use, the distal section 92 is rotated to a first position with one or more openings 54 on the lateral side facing in a first lateral direction. The fluid is moved through the passage 51 and is expelled through the one or more openings 54 on just the first lateral side. Because the opposing second lateral side does not include openings 54, no fluid is dispelled in that direction.

The user can then rotate the distal section 92 to a second position with the one or more openings 54 on the lateral side facing in the second lateral direction. Fluid can be moved through the passage 51 and expelled through the one or more openings on just the second lateral side.

In both the first and second positions, fluid can be expelled from the distal end 38 if the extension 32 includes one or more openings 54 on the distal end 38.

The selector 20 and nozzle 30 can be constructed from various materials, including but not limited to plastics and rubber. In one design, the extension 32 is flexible to facilitate insertion into the nasal cavity and prevent possible injury to the user.

The embodiments describe the device 10 being attached to a container 100, such as a bottle. The device 10 may also be attached to various other types of containers 100. Examples include but are not limited to a hose and a bag. The various containers 100 may be deformable by the user to force the fluid into the device 10, or may be non-deformable and require delivery to the device 10 in other manners such as gravity with the user tipping the container 100 to move the fluid into the device 10, and a pump that delivers the fluid from the container to the device 10.

Figure 12:
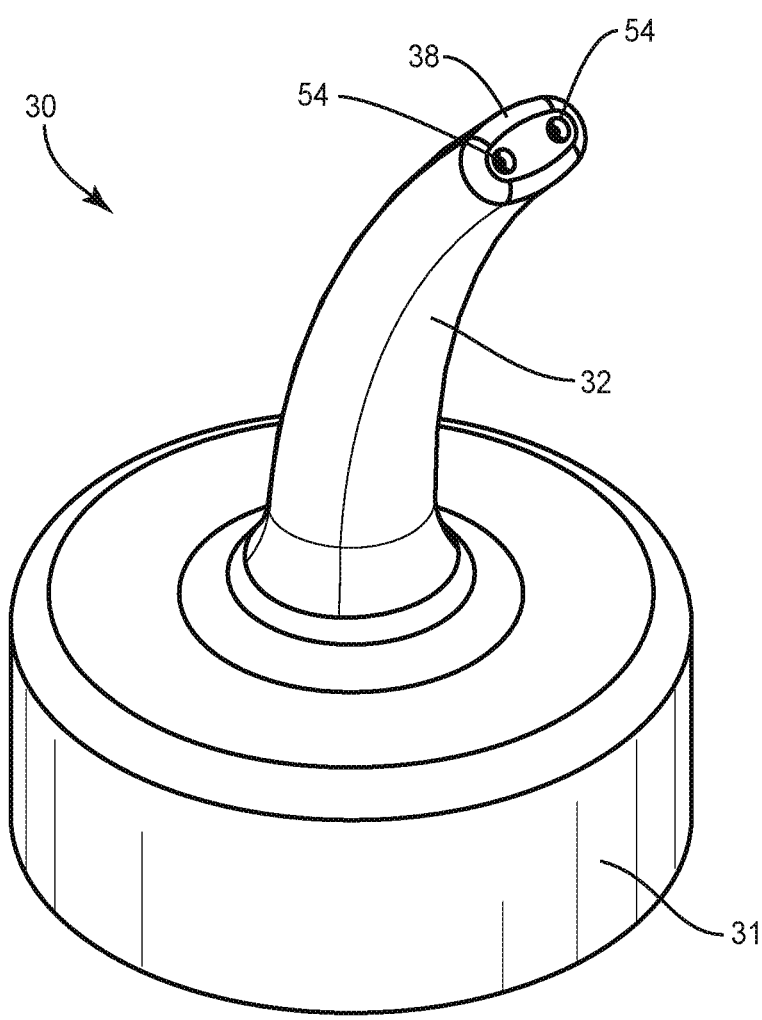
FIG. 12 is a perspective view of a nozzle.

As disclosed above, the device 10 can include openings 54 along the lateral sides of the nozzle 30. Openings 54 can also be positioned at the distal end 38. As illustrated in FIG. 12, the nozzle 30 can also include openings 54 at just the distal end 38 (i.e., there no openings 54 along the lateral sides of the nozzle 30). Each of the openings 54 can be aligned with one or more of the openings 54 at the distal end 38. In one design, a first opening 54 at the distal end 38 is aligned with the first passage 51 and a second opening 54 at the distal end 38 is aligned with the second passage 52. The selector 20 can be positioned at a first rotational position to expel fluid just through the first passage 51 and first opening 54, and positioned at a second rotational position to expel fluid through just the second passage 52 and the second opening 54.

The various devices 10 may be used during surgical procedures on living patients. These may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive.

What is claimed is:

1. A device to deliver fluid from a container to a nasal cavity, the device comprising:
  a selector comprising:
    a receptacle sized to extend over a top of the container and an opening sized to align with an outlet in the container; and
    a top face and a side wall that form the receptacle, with the opening extending through the side wall and the top face; and
  a nozzle connected to the selector, the nozzle comprising:
    first and second passages that are spaced apart and that each include a proximal end towards the selector and an opposing distal end;
    one or more first openings in communication with the first passage, the first openings positioned at a first lateral side of the nozzle; and one or more second openings in communication with the second passage, the second openings positioned at an opposing second lateral side of the nozzle;

the nozzle being rotatable relative to the selector between first and second positions;

the first position comprising the first passage aligned with the outlet in the container to receive the fluid from the container and deliver the fluid through the first passage and out through the one or more first openings and with the second passage positioned away from the outlet; and the second position including the second passage aligned with the outlet in the container to receive the fluid from the container and to deliver the fluid through the second passage and out through the second openings and with the first passage positioned away from the outlet.

2. The device of claim 1, wherein the first and second passages are fixedly positioned relative to each other within the nozzle.

3. The device of claim 1, wherein the nozzle comprises a base that connects to the selector and an extension that extends outward from the base in a direction away from the selector, the first and second passages extending through the extension.

4. The device of claim 3, wherein the extension comprises an elongated sectional shape with a major axis and a minor axis, the first and second passages being positioned along the major axis.

5. The device of claim 1, wherein the opening extends along the top face inward from the side wall and terminates at a back edge, the back edge being positioned away from a center point of the top face.

6. The device of claim 1, further comprising flanges that extend from each of the selector and the nozzle, wherein the flanges engage together to rotatably connect the selector to the nozzle.

7. The device of claim 1, further comprising filler rods positioned within each of the first passage and the second passage, the filler rods comprising smaller sectional sizes than the first passage and the second passage to limit an open area of the first passage and the second passage.

8. The device of claim 1, wherein the nozzle with a curved section with a length of 2-10 centimeters and has 30°-90° of curvature.

9. The device of claim 8, wherein the length of the curved section is between 3.75-4.25 centimeters and the curvature is 60°-80°.

10. The device of claim 1, further comprising a recess that extends into a distal end of the nozzle and the distal ends of the first and second passages terminate in the recess and are spaced inward from the distal end of the nozzle.

11. A device to deliver fluid from a container to a nasal cavity, the device comprising:

a selector and a nozzle that are connected together and configured to connect to the container;

the selector comprising an opening configured to align with an outlet in the container;

the nozzle comprising:
 a base and an outwardly-extending extension, the extension comprising a length measured between a proximal end at the base and an opposing distal end;
 a first passage that extends along the extension and comprises a first inlet at the base and first openings that face just towards the distal end and a first lateral side of the extension to expel the fluid from the first openings and to prevent the fluid from being expelled from a second lateral side of the extension; and
 a second passage spaced away from the first passage, the second passage extends along the extension and comprises a second inlet at the base and second openings that face just towards the distal end and the second lateral side of the extension to expel the fluid from the second openings and to prevent the fluid from being expelled from the first lateral side of the extension;

the nozzle being rotatable relative to the selector between a first position to align the first passage with the outlet in the container and the second passage being misaligned with the outlet, and a second position to align the second passage with the outlet in the container and the first passage being misaligned with the outlet; and filler rods positioned in the first and second passages to reduce an open interior space within the first and second passages.

12. The device of claim 11, further comprising a recess that extends into a distal end of the nozzle and the first and second passages terminate in the recess and are spaced inward from the distal end of the nozzle.

13. The device of claim 11, wherein the first position comprises the first inlet aligned with the outlet in the container to receive the fluid from the container and deliver the fluid through the first passage and out through the first openings, and the second position comprises the second inlet aligned with the outlet in the container to receive the fluid from the container and to deliver the fluid through the second passage and out through the second openings.

14. The device of claim 11, wherein the first passage and the second passage extend along the length of the extension in a side-by-side arrangement.

15. The device of claim 14, wherein the first passage and the second passage are fixedly positioned within the extension and remain stationary relative to each other in each of the first position and the second position.

16. The device of claim 14, wherein the extension comprises an elongated sectional shape with a major axis and a minor axis, the first and second passages being positioned along the major axis.

17. A method of delivering fluid from a container to a nasal cavity, the method comprising:

positioning a first filler rod within a first passage of a nozzle and reducing a size of the first passage prior to connecting a selector and the nozzle to the container;

positioning a second filler rod within a second passage of the nozzle and reducing a size of the second passage prior to connecting the selector and the nozzle to the container;

rotating the nozzle relative to the selector to a first position and aligning the first passage of the nozzle with an outlet of the container while the nozzle is connected to the selector and both the nozzle and the selector are connected to the container;

directing the fluid that is expelled from the container through the first passage that extends along the length of the nozzle and out through first openings that face outward towards a distal end and a first lateral side of the nozzle;

while in the first position, positioning the second passage of the nozzle away from the outlet and preventing the fluid from being moved into the second passage and preventing the fluid from being expelled outward from a second lateral side of the nozzle;

rotating the nozzle relative to the selector to a second position and aligning the second passage of the nozzle with the outlet of the container while the nozzle is connected to the selector and both the nozzle and the selector are connected to the container;

directing the fluid that is expelled from the container through the second passage that extends along the length of the nozzle and out through second openings that face outward towards the distal end and the second lateral side of the nozzle; and while in the second position, positioning the first passage of the nozzle away from the outlet and preventing the fluid from being moved into the second passage and preventing the fluid from being expelled outward from the first lateral side of the nozzle.

18. The method of claim 17, further comprising aligning a spout at the outlet of the container within a slot in the selector and connecting the selector and the nozzle to the container with the spout extending beyond the selector and being contained within the nozzle.

19. The method of claim 17, further comprising expelling the fluid from each of the first and second passages into a recess that extends into the distal end of the nozzle.

\* \* \* \* \*